United States Patent [19]

Sakanaka et al.

[11] Patent Number: 5,596,096

[45] Date of Patent: Jan. 21, 1997

[54] AZETIDINONE DERIVATIVES AND METHOD FOR PRODUCING AZETIDINONE AND CEPHALOSOPORIN DERIVATIVES

[75] Inventors: Osamu Sakanaka; Shouhei Yasuda, both of Yokohama; Shinjiro Sumi, Odawara; Katsufumi Sebata, Yokohama; Katsuharu Iinuma, Yokohama; Ken Nishihata, Yokohama, all of Japan

[73] Assignee: Meiji Seika Kaisha, Ltd., Tokyo, Japan

[21] Appl. No.: 282,005

[22] Filed: Jul. 29, 1994

Related U.S. Application Data

[63] Continuation of Ser. No. 836,527, Feb. 18, 1992, abandoned, and a division of Ser. No. 76,195, Jun. 14, 1993, Pat. No. 5,405,955, which is a division of Ser. No. 836,527.

[30] Foreign Application Priority Data

Feb. 20, 1991 [JP] Japan .................... 3-109904
Feb. 20, 1991 [JP] Japan .................... 3-109906

[51] Int. Cl.$^6$ .......................................... C07D 513/04
[52] U.S. Cl. .................................................. 540/352
[58] Field of Search ....................................... 540/352

[56] References Cited

U.S. PATENT DOCUMENTS

| | | | |
|---|---|---|---|
| 3,862,164 | 1/1975 | Cooper | 540/352 |
| 3,900,487 | 8/1975 | Underwood et al. | 260/306.7 C |
| 4,422,971 | 12/1983 | Akkerboom | 540/346 |
| 4,689,411 | 8/1987 | Torii et al. | 540/358 |
| 4,740,590 | 4/1988 | Torii et al. | 540/358 |
| 4,798,890 | 1/1989 | Torii et al. | 540/358 |
| 4,810,788 | 3/1989 | Torii et al. | 540/353 |
| 5,132,419 | 7/1992 | Lanz | 540/215 |
| 5,162,524 | 11/1992 | Farina et al. | 540/358 |
| 5,206,361 | 4/1993 | Torii et al. | 540/352 |
| 5,266,691 | 11/1993 | Farina et al. | 540/230 |

FOREIGN PATENT DOCUMENTS

0122002 10/1984 European Pat. Off. .
2504927 5/1982 France .

OTHER PUBLICATIONS

Eagle et al. "The Rearrangement of p–Nitrobenyl 2R–(1R, 5R)–3–Benzylidene–4–Formyl–6–Oxo–4, 7–Diaza–2–Thiabicyclo (3, 2, 0) Heptan–7–yl)–3–Methylbut–3–Enoate 2'–Oxide" in Tetrahedron Letters, No. 47, pp. 4703–4706, Pergamon Press 1978. Month of publication not provided.

Sigeru Torii et al. "Penicillin–Cephalosporin Conversion III. A Novel Route to 3–Chloromethyl–$\Delta^3$–Cephans" in Tetr. Letters, vol. 23, No. 21, pp. 2187–2188, Month of publication not provided 1982.

Search Report in EPO Appln. No. 92102776.9 mailed Sep. 4, 1992.

*Primary Examiner*—Mukund J. Shah
*Assistant Examiner*—King Lit Wong
*Attorney, Agent, or Firm*—Varndell Legal Group

[57] ABSTRACT

New compounds are disclosed having the general formulas (1) and (2):

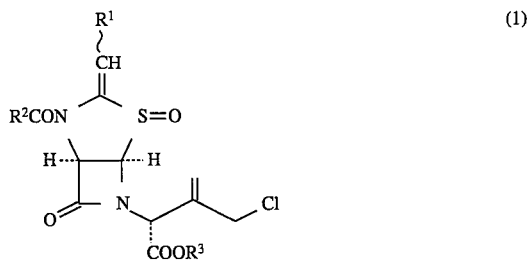

Also described is a process for preparing the compounds of formulas (1) and (2). Further described is a process for preparing a cephalosporin derivative having formula (5):

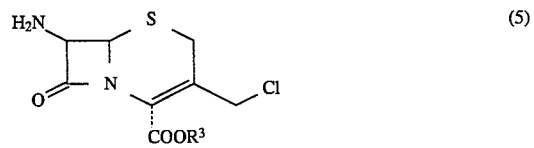

by converting the compound of formula (1) to the compound of formula (2) and then converting the compound of formula (2) to the compound of formula (5).

5 Claims, No Drawings

AZETIDINONE DERIVATIVES AND METHOD FOR PRODUCING AZETIDINONE AND CEPHALOSOPORIN DERIVATIVES

CROSS-REFERENCE TO RELATED APPLICATION

This application is a divisional application of U.S. Ser. No. 08/076,195, filed Jun. 14, 1993, now U.S. Pat. No. 5,405,955, which is divisional application of U.S. Ser. No. 07/836,527, filed Feb. 18, 1992, now abandoned. This application is a continuation application of U.S. Ser. No. 07/836,527, filed Feb. 18, 1992, now abandoned.

FIELD OF THE INVENTION

The present invention is directed to azetidinone derivatives having the general formulas (1) and (2) as set forth below:

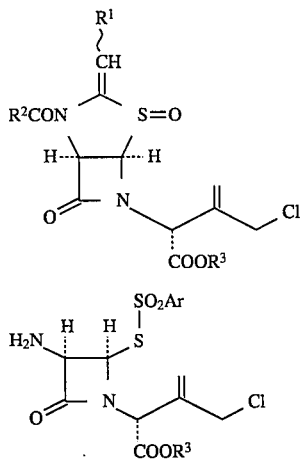

In the thiazolidine-azetidinone derivatives expressed by general formula (1) above. $R^1$ can be a substituted aryl group, an unsubstituted aryl group, a substituted aryloxy group and an unsubstituted aryloxy group; $R^2CO$ can be a carboxyl residue; and $R^3$ can be a hydrogen atom or carboxylic protective group.

In the azetidinone derivatives expressed by the general formula (2) above, $R^3$ can be a hydrogen atom or a carboxylic protective group, and Ar can be an unsubstituted or substituted aryl group.

The present invention is also directed to methods of preparing azetidinone derivatives expressed by general formulas (1) and (2), as well as methods of using these azetidinone derivatives to prepared cephalosporin derivatives such as those expressed by general formula (5) below:

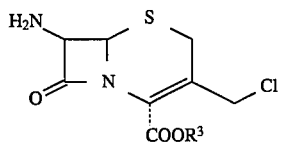

(where $R^3$ has already been defined).

BACKGROUND OF THE INVENTION

It is known that the cephalosporin derivatives represented by compound (5) are important intermediates that can readily be transformed into various types of cephalosporin antibiotics, such as cefazolin, cefmetazole, cefamandole, cefotiam, cefmenoxime, ceftriaxone. ceibuperazone, cefuzonam and cefminox. This can be accomplished by a processes such as acylation of the ammo group at the 7 position, substitution of the chloromethyl group at the 3 position with an aromatic heterocyclicthiol, and removal of the carboxylic protective group. Therefore, the compound (5) is valued highly in industry.

Chloro compounds are known in the art. Examples are those cited by R. D. G. Cooper (Tetrahedron Lett., 21, 781 (1980)) and by Shigeru Torii and ethers (Japanese Unexamined Patent Publication Nos. 57-59896, 57-59897, and 59-55888). These examples concern thiazolidine azetidinone derivatives represented by formula (6):

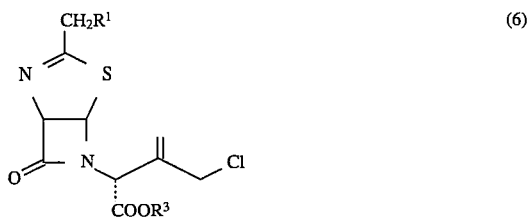

The chloro compounds of formula (6) differ from the thiazolidine azetidinone derivatives of the present invention which are a totally new compounds.

Other known chloro derivatives include those shown by Torii, et al. (Japanese Unexamined Patent Publication Nos. 58-85894 and 59-164771). These derivatives are expressed by the general formula (7) below. These derivatives all include a form where the amino groups are protected by acyl groups as shown in formula (7) below:

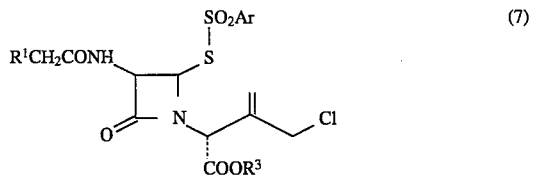

Thus, an extra process of disconnecting this acyl group becomes necessary at the end of the process. The present invention requires no such extra process.

SUMMARY OF THE INVENTION

An object of the present invention is to efficiently prepare thiazolidine-azetidinone derivatives, whose methyl groups at the allylic position can be chlorinated, as shown in general formula (1), by a simple process of chlorination of the methyl groups of the allyl position of the thiazolidine-azetidinone derivatives, which are expressed by general formula (3) as shown below. An additional objective of the present invention is the transformation of this synthetic intermediate (1) into azetidinone derivatives expressed by general formula (2), which a synthetic precursor for the cephalosporin derivative (5), at a high yield by applying a simple method.

DETAILED DESCRIPTION OF THE INVENTION

The thiazolidine-azetidinone expressed by general formula (1):

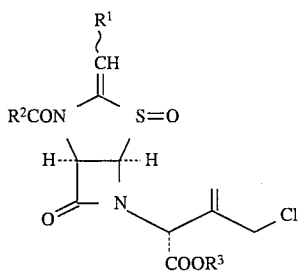
(1)

(where $R^1$, $R^2$, and $R^3$ already have been defined) can be produced through a reaction between a chlorinating agent and a thiazolidine azetidinone derivative defined by general formula (3) in an organic solvent:

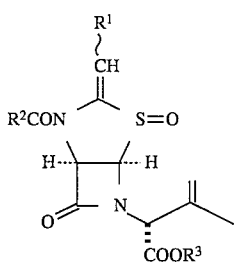
(3)

where $R^1$ is a substituted aryl group, an unsubstituted aryl group, a substituted aryloxy group, and an unsubstituted aryloxy group; $R^2CO$ is a carboxyl residue, and $R^3$ is a hydrogen atom or carboxylic protective group.

The azetidinone derivatives expressed by general formula (2):

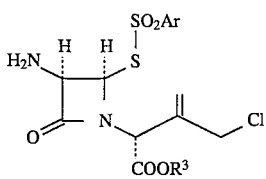
(2)

(where $R^3$ and Ar have already been defined) can be produced through a reaction between the compound of general formula (1) and an arylsulfinic acid expressed by general formula (4):

Ar—SO$_2$H (4)

(where Ar has already been defined) in the presence of an acid in an organic solvent that contains a lower alcohol, The thiazolidine-azetidinone derivatives (1) and the azetidinone derivatives (2) are not known and have not been described in the prior art, Thiazolidine-azetidinone derivatives expressed by general formula (1) and azetidinone derivatives expressed by general formula (2) are Important intermediates of cephalosporin antibiotics and can be transformed into cephalosporin derivatives (5) as shown in following reaction scheme (A):

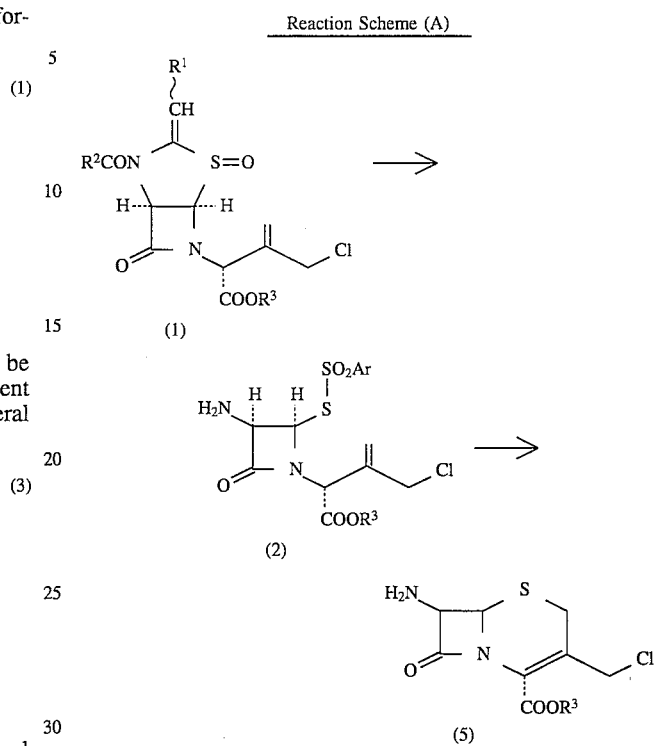

where $R^1$, $R^2$, $R^3$ and Ar are defined above.

The reaction conditions for transforming the thiazolidine-azetidinone derivative of formula (1) into the azetidinone derivative of formula (2) is described elsewhere in this application. The compound represented by formula (2) can be convened into the compound represented by formula (5) by reaction in the presence of a base. For example, compound (2) can be added to a solvent containing a base having a molar quantity of about 1.1 to about 1.5 relative to compound (2). The reaction can be carried out at a temperature from about −50° C. to 5° C. for about 5 to about 30 minutes. Suitable bases include ammonia, ammonia water, potassium hydroxide, sodium hydroxide, potassium acetate, sodium acetate, triethylamine, pyridine, 1,8-diazabicyclo [5.4.0]undec-7-ene, 1,5-diazabicyclo[4.3.0]non-5 ene, potassium iodide and sodium iodide. Suitable solvents include dimethylformamide, dimethylacetamide, methanol, ethanol, 2-propanol, acetonitrile, butylonitrile, acetone and methyl ethyl ketone.

The starting material (3) used in the present invention is a compound that can be readily synthesized from penicillin sulfoxide (8), as shown in reaction scheme (B). Specifically, compound (8) is transformed into compound (9) by a method proposed by R. D. G. Cooper, et al. (J. Am. Chem. Soc., 92, 2575 (1970)) and compound (3) from compound (9) via compound (10) by a method cited by S. J. Eagle, et al. (Tetrahedron Lett., 1978, 4703).

Reaction Scheme (B)

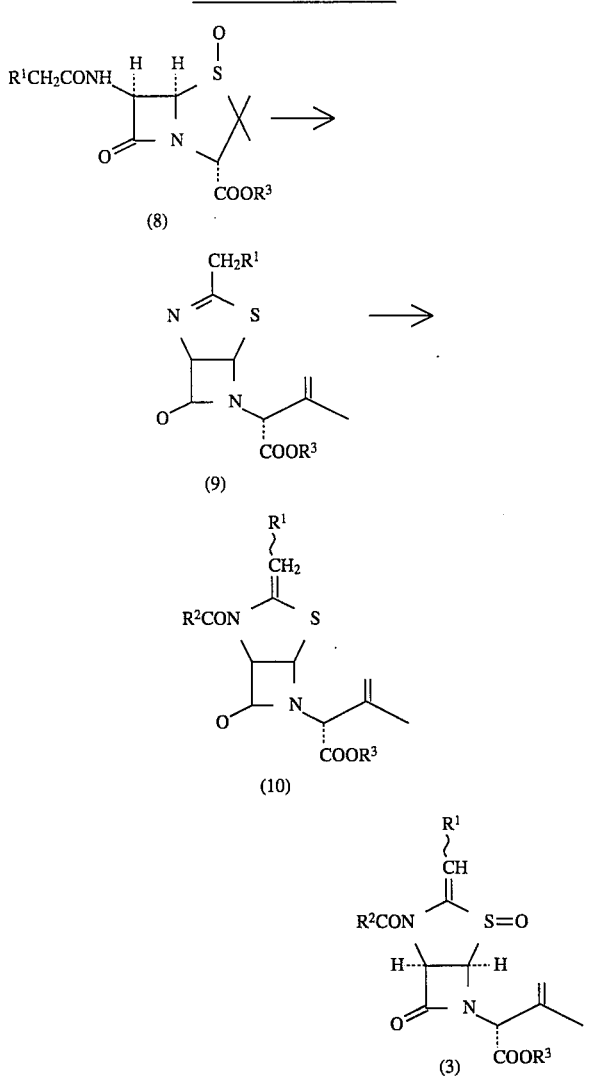

For example, a compound represented by formula (8), penicillin sulfoxide can be reacted with trimethyl phosphite in refluxing benzene for a period of time such as 30 hours to obtain a compound represented by formula (9). The compound (9) can be acylated (e.g., in a Ac₂O/HCOOH reaction medium) to give the compound represented by formula (10) in high yields. Oxidation of compound (10) with peracetic acid ($CH_3CO_3H$) provides a quantitative yield of the compound represented by formula (3).

For the thiazolidine azetidinone derivatives (3) and (1) used in the present invention, no particular restrictions are placed on $R^1$, $R^2$, and $R^3$ and the protection groups which are commonly used in penicillin-cephalosporin conversion are applicable. Examples of $R^1$ include aryl groups such as phenyl, paranitrophenyl, and parachlorophenyl groups with or without substitutions or substituents. Examples of $R^2$ include an hydrogen atom and lower alkyl groups such as methyl group, ethyl group, and n-butyl group; and aryl groups such as phenyl, paratolyl, paranitrophenyl, and parachlorophenyl groups with or without substitutions or substituents. Examples of $R^3$ include phenylmethyl groups such as benzyl, paranitrobenzyl, paramethoxybenzyl, and diphenylmethyl groups with or without substitutions or substituents; and low alkyl groups such as methyl, ethyl, tertiary butyl, with or without halogen substituents, such as 2,2,2-trichloroethyl.

In the method of the present invention where the methyl group at the allyl position is chlorinated in the process of converting the compound represented by formula (3) to the compound represented by formula (1), the thiazolidine azetidinone derivative (3) is dissolved in an organic solvent at a concentration of 1 mol/1 liter to 0.01 mol/1 liter, followed by a reaction of a chlorinating agent. Any suitable chlorinating agent can be used, such as tertiary butyl hypochlorite and chlorine gas. Between these two tertiary butyl hypochlorite is particularly desirable. The reaction temperature and reaction time vary according to the particular thiazolidine azetidinone derivatives (3) reacted and the chlorinating agents used; but the temperature is usually set between −60° and 20° C., or more preferably between −30° to 10° C., and the reaction is usually completed between 10 minutes to 2 hours. When tertiary butyl hypochlorite is used as the chlorinating agent, the reaction is enhanced by the addition of acids, such as hydrochloric acid and p-toluenesulfonic acid. When chlorine gas is used, it is recommend to add inorganic bases such as sodium hydrogen carbonate, potassium carbonate, and calcium oxide or propylene oxide as acid capturing agents.

Examples for organic solvents used in above method for converting the compound of formula (3) to the compound of formula (1) of the present invention are lower alcohols such as methanol, ethanol, and isopropanol; ethers such as diethyl ether, diisopropyl ether, tetrahydrofuran, and 1,4-dioxane; halogenated hydrocarbon solvents such as dichloromethane, chloroform, and 1,2-dichloroethane; and esters such as ethyl acetate and methyl formate.

For the method of the present invention where thiazolidine-azetidinone derivative represented by formula (1) is transformed into azetidinone derivative represented by formula (2), the former is dissolved in an organic solvent containing a lower alcohol (such as methanol) at a concentration of 1 mol/1 liter to 0.01 mol/1 liter. To this solution, an acid (such as hydrochloric acid) and the arylsulfinic acid of formula (4) or its metallic salt are added and a reaction is carried out. The reaction temperature and reaction time are dependent on the type of thiazolidine azetidinone derivative (1) reacted. However, a range of −20° to 50° C. (preferably or −5° to 25° C.) is desirable. The reaction is normally completed within 30 minutes to 10 hours. The quantity of arylsulfinic acid (4) usually used ranges from 1.0 to 5.0 times (preferably from 1.05 to 1.20 times) the quantity of thiazolidine-azetidinone derivative (1). Representative acids for addition to the reaction include mineral acids such as hydrochloric acid, sulfuric acid, and phosphoric acid; and organic acids such as trifluoroacetic acid, methanesulfonic acid, and paratoluenesulfonic acid. Preferable among these acids are 1 to 20% methanolmethanesulfonic acid and 1 to 20% methanol-hydrochloric acid. The quantity of the acid added ranges from 0.1 to 20 times, or more preferably from 5 to 10 times, the quantity of thiazolidine-azetidinone (1).

For the organic solvent, a lower alcohol or a mixed solvent containing at least ene type of lower alcohol is used. Examples of lower alcohols include methanol, ethanol, and n-butanol. Examples of the organic solvents mixed with lower alcohols are ketones such as acetone and methyl ethyl ketone; nitriles such as acetonitrile and butylonitrile; ethers such as diethyl ether, diisopropyl ether, tetrahydrofuran, chloroform, and 1,4-dioxane; halogenated hydrocarbon solvents such as nitromethane, dichloromethane, chloroform, 1,2-dichloroethane, and carbon tetrachloride; aromatic solvents such as benzene, toluene, and chlorobenzene; esters such as ethyl acetate and methyl formate; and amides such as dimethylformamide and dimethylacetamide.

The compounds of the present invention, which have been produced by the above-described method, are readily isolated and purified by a standard isolation procedures.

EXAMPLE 1

This example describes the preparation of p-methoxybenzyl 2R-[(1R, 5R)-3-benzyliden-4-formyl-6-oxo-4, 7-diaza-2-thiabicyclo[3. 2. 0]heptan-7-yl]-3-chloromethyl-3-butenoate 2'-oxide (1a) (the compound of formula (1) where $R^1$=phenyl, $R^2$=hydrogen and $R^3$=p-methoxybenzyl).

Five grams of compound (3a) (the compound of formula (3) where $R^1$=phenyl, $R^2$=hydrogen and $R^3$=paramethoxybenzyl) was dissolved in 150 ml of methyl formate and cooled to −20° C. To this solution, 2.0 ml of t-butyl hypochlorite was added gradually and a reaction was allowed to take place at a temperature range of −20° to −10° C. for 30 minutes. The reaction fluid was diluted in 200 ml of ethyl acetate, washed 3 times in 200 ml of water, dried using sodium sulfate anhydride, and condensed in vacuum. The residue was purified using column chromatography (acetonitrile-water, 3:2) with reversed phase $C_{18}$ (Nakaraitesuku Cosmoseal $75C_{18}$OPN, 500 g). Compound (1a) amounting to 4.75 g (88.8%) in a white powder form was obtained.

$^1$H-NMR (CDCl$_3$) δ3.64 (s, 2H, CH$_2$Cl), 3.78 (s, 3H, OCH$_3$), 5.04, 5.03, 5.28 (each s, each 1H, C$\underline{H}$ (COOCH$_2$C$_6$H$_4$OCH$_3$) C (CH$_2$Cl)=C$\underline{H}_2$), 5.07 (d, 1H, J =11.7Hz, CH$_2$C$_6$H$_4$OCH$_3$), 5.15 (d, 1H, J =11.7Hz, CH$_2$C$_6$H$_4$OCH$_3$), 5.44 (d, 1H, J=4.0 Hz, β-lactam), 6.16 (d, 1H, J=4.0Hz, β-lactam), 6.86 (d, 2H, J=8.8Hz, CH$_2$C$_6$H$_4$OCH$_3$), 7.24 (d, 2H, J=8.8 Hz, CH$_2$C$_6$H$_4$OCH$_3$), 7.44–7.57 (m, 6H, =CHC$_6$H$_5$) 8.47 (s, 1H, HCO)

IR 1785, 1740, 1690 cm$^{-1}$.

EXAMPLE 2

This example describes the preparation of p-methoxybenzyl 2R-[(1R, 5R)-3-benzyliden-4-acetyl-6-oxo-4, 7-diaza-2-thiabicyclo[3. 2. 0]heptan-7-yl]-3-chloromethyl-3-butenoate 2'-oxide (1b) (the compound of formula (1) where $R^1$=phenyl, $R^2$=methyl and $R^3$=p-methoxybenzyl)

Five grams of compound (3b) (the compound of formula (3) where $R^1$=phenyl, $R^2$=methyl, $R^3$=p-methoxybenzyl) was dissolved in 150 ml of methyl formate and cooled to −50° C. To this solution, 2.2 ml of t-butyl hypochlorite was gradually added and a reaction was allowed to place at −50° to −40° C. for 60 minutes. Through a procedure similar to that described in Example 1, 4.65 g (87.3%) of compound (1b) was obtained in a white powder form.

$^1$H-NMR (CDCl$_3$) δ2.35 (s, 3H, CH$_3$CO), 3.49 (s, 2H, CH$_2$Cl), 3.89 (s, 3H, OCH$_3$), 5.02, 5.20 (each s, 2H, 1H, C$\underline{H}$ (COOCH$_2$C$_6$H$_4$OCH$_3$) C (CH$_2$Cl)=C$\underline{H}_2$), 5.09 (d, 1H, J=11.7Hz, CH$_2$C$_6$H$_4$OCH$_3$). 5.15 (d, 1H, J=11.7Hz, CH$_2$C$_6$H$_4$OCH$_3$), 5.34 (d, 1H, J=4.0Hz, β-lactam), 6.37 (d, 1H, J=4.0Hz, β-lactam), 6.87 (d, 2H, J=8.8Hz, CH$_2$C$_6$H$_4$OCH$_3$), 7.24 (d, 2H, J=8.8Hz, CH$_2$C$_6$H$_4$OCH$_3$), 7.38 (s, 1H, =C$\underline{H}$C$_6$H$_5$), 7.40–7.65 (m, 5H, =CHC$_6$$\underline{H}_5$)

IR 1785, 1740, 1690 cm$^{-1}$.

EXAMPLE 3

Synthesis of Compound (1a)

Two grams of compound (3a) was dissolved in 100 ml of methylene chloride and cooled to 0° C. To the solution, 0.5 ml of 1N-hydrogen chloride/methanol and then 0.8 ml of t-butyl hypochlorite were added and a reaction was allowed to take place at a temperature range of 0° to 5° C. for 30 minutes. Procedures similar to those described in Example 1 were conducted to obtain 1.79g (83.7%) of compound (1a).

EXAMPLE 4

Compound (3a), 7.8 g, was dissolved in 150 ml of dioxane. To the solution, 4.4 ml of propylene oxide was added and the mixture was cooled to 10° C. Over the solution, 22 ml of a carbon tetrachloride solution of chlorine (concentration at 1.8M) was gradually dripped therein. After a reaction at a temperature range of 10° to 12° C. for 5 hours, the reaction fluid was condensed in vacuum without further processing. The residue was purified by procedures similar to those described for Example 1 to obtain 4.34 g (52.1%) of compound (1a).

EXAMPLE 5

This example describes the preparation of p-methoxybenzyl 2-(3-amino-4-(p-toluene)sulfonylthio-2-azetidinon-1-yl)-3-chloromethyl-3butenoate (2a) (the compound of formula (2) where $R^1$=p-methoxybenzyl and Ar=p-tolyl).

First, 500 mg of compound (1a) ($R^1$=phenyl, $R^2$=hydrogen, $R^3$=p-methoxybenzyl) was dissolved in a mixture of 1.5 ml of methylene chloride and 10 ml of methanol. While being chilled, 1 ml of 6N-hydrochloric acid and 166 mg of paratoluenesulfonic acid were added to the solution and a reaction was allowed to take place at ambient temperature for 4 hours. The reaction fluid was poured into a mixture of 50 ml of methylene chloride and 50 ml of water. Following fluid separation, the aqueous layer was extracted in 10 ml of methylene chloride and combined with the organic layer, which was then dried by using sodium sulfate anhydride and condensed in vacuum. The residue was purified using column chromatography (acetonitrile-water 3:2) with reversed phase $C_{18}$ (Nakaraitesuku Cosmoseal 75 $C_{18}$OPN, 50 g), which resulted in the production of 428 mg (84%) of compound (2a) in the form of light yellow syrup.

$^1$H-NMR (CDCl$_3$) δ1.78 (bs, 2H, NH$_2$), 2.44 (s, 3H, SO$_2$C$_6$H$_4$CH$_3$), 3.80 (s, 3H, CH$_2$C$_6$H$_4$OCH$_3$), 4.07 (s, 2H, CH$_2$C$_6$H$_4$OCH$_3$). 4.63 (d, 1H, J=4.5 Hz, β-lactam), 4.93, 5.07, 5.37 (each s, each 1H, C$\underline{H}$ (COOCH$_2$C$_6$H$_4$OCH$_3$) C (CH$_2$Cl)=C$\underline{H}_2$), 5.10 (d, 1H, J=10.8Hz, CH$_2$Cl), 5.17 (d, 1H, J=10.8Hz, CH$_2$Cl), 5.53 (d, 1H, J=4.5Hz, β-lactam), 6.89 (d, 2H, J=9.0Hz, CH$_2$C$_6$H$_4$OCH$_3$), 7.28 (d, 2H, J=9.0 Hz, CH$_2$C$_6$H$_4$OCH$_3$), 7.33 (d, 2H, J=8.4Hz, SO$_2$C$_6$H$_4$CH$_3$), 7.77 (d, 2H, J=8.4Hz, SO$_2$C$_6$H$_4$CH$_3$)

IR 3400, 3340, 1775, 1740, 1335, 1145 cm$^{-1}$.

EXAMPLE 6

This example describes the preparation of p-methoxybenzyl 2-(3-amino-4-benzenesulfonylthio-2-azetidinon-1-yl)-3-chloromethyl-3-butenoate (2b) (the compound of formula (2) where $R^1$=p-methoxybenzyl and Ar=phenyl).

First, 500 mg of compound (1a) ($R^1$-phenyl, $R^2$=hydrogen, $R^3$=p-methoxybenzyl) was dissolved in a mixture of 1.5 ml of methylene chloride and 4 ml of methanol. Winkle the solution was chilled, 6 ml of 1N-hydrogen chloride/methanol and 213 mg of sodium benzenesulfinate dihydrate were added and a reaction was allowed to take place at ambient for 3 hours. Procedures similar to those of Example 1 were conducted to obtain 443 mg (87%) of compound (2b) in the form of a light yellow syrup.

$^1$H - NMR (CDCl$_3$) δ1.80 (bs, 2H, NH$_2$), 3.80 (s, 3H, CH$_2$C$_6$H$_4$OCH$_3$), 4.05 (s, 2H, CH$_2$C$_6$H$_4$OCH$_3$), 4.63 (d, 1H, J=4.5Hz, β-lactam), 4.92, 5.01, 5.33 (each s, each 1H, CH(COOCH$_2$C$_6$H$_4$OCH$_3$)C(CH$_2$Cl)=CH$_2$), 5.09 (d, 1H, J=10.8Hz, CH$_2$Cl), 5.16 (d, 1H, J=10.8Hz, CH$_2$Cl), 5.55 (d, 1H, J=4.5 Hz, β-lactam), 6.89 (d, 2H, J=9.0Hz, CH$_2$C$_6$H$_4$OCH$_3$), 7.28 (d, 2H, J=9.0Hz, CH$_2$C$_6$H$_4$OCH$_3$), 7.51–7.89 (5h, m, SO$_2$C$_6$H$_5$)

IR 3400, 3340, 1775, 1740, 1335, 1145 cm$^{-1}$.

EXAMPLE 7

This example describes the preparation of p-methoxybenzyl 2-(3-amino-4-benzenesulfonylthio-2-azetidinon-1-yl)-3-chloromethyl-3-butenoate (2b) (R$^1$=p-methoxybenzyl, Ar=phenyl)

One gram of compound (1b) (R$^1$=phenyl, R$^2$=methyl, R$^3$=p-methoxybenzyl) was dissolved in a mixture of 3 ml of methylene chloride and 8 ml of methanol. While the solution was being chilled, 12 ml of 1N-hydrogen chloride/methanol and 450 mg of sodium benzenesulfinate dihydrate were added and a reaction was allowed to take place at ambient for 12 hours. Procedures similar to those of Example 1 were performed to obtain 797 mg (82%) of compound (2b).

EXAMPLE 8

This example describes the preparation of p-methoxybenzyl 2-(3-amino-4-(p-toluene)sulfonylthio-2-azetidinon-1-yl)-3-chloromethyl-3-butenoate (2a).

First, 750 mg of compound (1a) (R$^1$=phenyl, R$^2$=hydrogen, R$^3$=p-methoxybenzyl) was dissolved in a mixture of 2.3 ml of methylene chloride and 15 ml of methanol. While the solution was being chilled, 0.331 ml of methanesulfonic acid and 686 mg of sodium benzenesulfinate were added and a reaction was allowed to take place at the same temperature for 18 hours. The reaction fluid was added to a mixture of 75 ml of methylene chloride and 75 ml of water. After separation of the fluid, the organic layer was dried using anhydrous sodium sulfate and condensed in vacuum. The residue was purified by using column chromatography (acetonitrile-water 3:2) with reversed phase C$_{18}$ (Nakaraitesuku Cosmoseal 75 C$_{18}$ OPN, 80 g). Compound (2a) in a quantity of 686 mg (91%) was obtained in the form of a light yellow syrup.

Thiazolidine azetidinone derivatives expressed by general formula (1) and azetidinone derivatives expressed by general formula (2) of the present invention are easily transformed into important synthetic intermediates (5) of various cephalosporins via aforementioned reaction scheme (A) which was introduced by the present inventors. For this reason, the present invention is extremely valuable in the pharmaceutical industry. Furthermore, inexpensive penicillins may be used as the starting material, which contributes significantly to a reduction in the manufacturing costs of various cephalosporin antibiotics.

We claim:

1. A thiazolidine azetidinone represented by the formula (1):

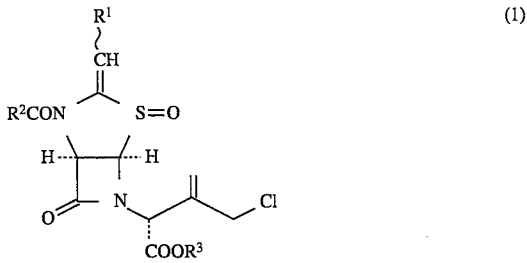

wherein R$^1$ is a member selected from the group consisting of a substituted aryl group, an unsubstituted aryl group, a substituted aryloxy group and an unsubstituted aryloxy group; R$^2$CO is a carboxyl residue, and R$^3$ is member selected from the group consisting of hydrogen atom and carboxylic protective group.

2. The thiazolidine azetidinone derivative of claim 1, wherein R$^1$ is selected from the group consisting of unsubstituted aryl and unsubstituted aryloxy.

3. The thiazolidine azetidinone derivative of claim 1, wherein R$^1$ is phenyl, R$^2$ is hydrogen and R$^3$ is p-methoxybenzyl.

4. The thiazolidine azetidinone derivative of claim 1, wherein R$^1$ is phenyl, R$^2$ is methyl, and R$^3$ is p-methoxybenzyl.

5. A thiazolidine azetidinone represented by the formula (1):

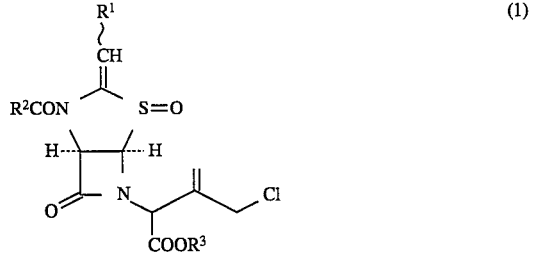

wherein R$^1$ is a member selected from the group consisting of phenyl, paranitrophenyl and parachlorophenyl; R$^2$ is a member selected from the group consisting of hydrogen, methyl, ethyl, n-butyl, phenyl, paratolyl, paranitrophenyl and parachlorophenyl; and R$^3$ is a member selected from the group consisting of benzyl, paranitrobenzyl, paramethoxybenzyl, diphenylmethyl, methyl, ethyl, tertiary butyl, and 2,2,2-trichloroethyl.

* * * * *